United States Patent [19]

Krimmel

[11] 4,051,136
[45] Sept. 27, 1977

[54] PIPERAZINYL CYCLOBUTENONES

[75] Inventor: Carl Peter Krimmel, Wauconda, Ill.

[73] Assignee: G. D. Searle & Co., Chicago, Ill.

[21] Appl. No.: 674,519

[22] Filed: Apr. 7, 1976

[51] Int. Cl.$^2$ .................. C07D 295/02; C07D 243/08
[52] U.S. Cl. ......................... 260/268 R; 260/268 BC; 260/268 B; 424/250; 424/244
[58] Field of Search .......... 260/268 R, 268 B, 239 BC

[56] References Cited
PUBLICATIONS

H. E. Sprenger et al. Angew. Chem. Int. Ed. Eng. 1968, vol. 7 (7), 530–535.

*Primary Examiner*—Donald G. Daus
*Assistant Examiner*—Jose Tovar
*Attorney, Agent, or Firm*—John J. Kolano

[57] ABSTRACT

1-[2-Hydroxy-3-(4-alkyl-1-piperazinyl)-4-oxo-2-cyclobuten-1-ylidene]-4-alkylpiperazinium hydroxide inner salts and related compounds are described herein. These compounds are useful as anti-viral agents. They are prepared from 2-anilino-3-hydroxy-4-(phenylimino)-2-cyclobuten-1-one and the appropriate monosubstituted piperazine.

5 Claims, No Drawings

PIPERAZINYL CYCLOBUTENONES

The present invention relates to a group of compounds which are piperazinyl cyclobutenones. More particularly, it relates to a group of compounds having the following general formula.

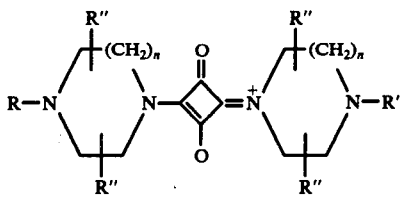

wherein R and R' are alkyl containing from 2 to 6 carbon atoms; R" is hydrogen or methyl; and n is one or two. It should be noted that the structure given above is one of four equivalent canonical structures that can be written for the compounds of the present invention.

As indicated above, the alkyl groups contain from 2 to 6 carbon atoms. These alkyl groups can be straight chain or branched and are exemplified by ethyl, propyl, isopropyl, butyl, and hexyl.

The organic bases of this invention form pharmaceutically acceptable acid addition salts with a variety of organic and inorganic acids. Such salts are formed with acids such as sulfuric, phosphoric, hydrochloric, hydrobromic, hydroiodic, sulfamic, citric, lactic, maleic, malic, succinic, tartaric, cinnamic, acetic, benzoic, gluconic, ascorbic, and related acids.

The compounds of the present invention are conveniently prepared by the reaction of an appropriate 1-alkylpiperazine with an anilinocyclobutenone having the following formula

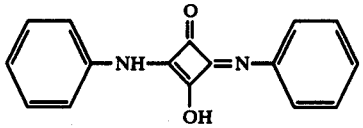

The reaction is carried out neat with heating at about 190°–220° C. While the necessary anilinocyclobutenone starting material is known, the procedures for its preparation which appear in the literature give a mixture of isomers. However, it has now been found that, if squaric acid is reacted with aniline using pyridine as the solvent and the product is washed with dimethylformamide, the desired 2,4-isomer is obtained in high purity. Alternatively, it is also possible to obtain the compounds of the present invention by the direct reaction of squaric acid with a 1-alkylpiperazine.

The compounds of the present invention are useful as anti-viral agents. In particular, the present compounds have been found active against influenza A (strain 575) virus and Herpesvirus homimis type 2 strain MS. The present compounds can thus be combined with various known excipients and adjuvants in the form of dusts, solutions, suspensions, ointments and sprays to provide compositions useful for disinfecting purposes, such as for laboratory equipment.

The anti-viral utility of the instant compounds is evident from the results of a standardized test to determine their anti-viral activity. This activity is determined by the following test procedure.

Cell cultures of primary Rhesus monkey kidney maintained in 25 cm² plastic flasks and each containing test compound at concentrations of 625, 125, 25, 5, or 1 microgram per milliliter are prepared in pairs. These flasks, and an identical pair of flasks containing no test compound, are each innoculated with a dose of influenza virus type A (strain 575) previously shown to produce maximum hemadsorption and minimum cytopathogenic effects after a 24 hour incubation. Where the cultures contain test compound, the virus is added one hour after addition of the compound to the culture. After 24 hours incubation of the cultures, the supernatant fluids are removed and 4.0 ml. of a 0.4% suspension of guinea pig erythrocytes are added to each flask. The flasks are then incubated at 4° C in a horizontal position for 30 minutes. The flasks are rocked every 10 minutes during the incubation period. After this incubation, the red cell suspension is decanted from each flask, the flasks are washed twice with 4.0 ml. of phosphate buffer saline solution (pH 7.4) to remove unadsorbed red cells, and 4.0 ml. of distilled water is then added to lyse the adsorbed cells. The flasks are then further incubated at 37° C. for 30 minutes in a horizontal position and the flasks are rocked every 10 minutes. After this incubation, the fluid contents of the pairs of flasks are combined to form an assay unit and are placed at room temperature for 15–30 minutes to allow settling of cellular debris. A pair of control flasks identical with the above, except for the absence of test compound and virus inoculation, is run concurrently. The resulting hemoglobin solutions from each assay unit are then read for optical density in a spectrophotometer. A test compound is considered active if, at one of the tested levels, it reduces the optical density reading by at least 50% relative to the virus control. The optical densities observed are further used to calculate the concentration of test compound which would produce a 50% reduction in the optical density reading. When 1-[2-hydroxy-3-(4-ethyl-1-piperazinyl)-4-oxo-2-cyclobuten-1-ylidene]-4-ethylpiperazinium hydroxide inner salt and 1-[2-hydroxy-3-(4-propyl-1-piperazinyl)-4-oxo-2-cyclobuten-1-ylidene]-4-propylpiperazinium hydroxide inner salt were tested by the above procedure, they were found to be active as anti-viral agents.

The following examples are presented to further illustrate the present invention: they should not be construed as limiting it in spirit or in scope. In these examples, temperatures are indicated in degrees centigrade (° C.), quantities by weight are indicated in grams and quantities by volume are indicated in mililiters.

EXAMPLE 1

A mixture of 2.6 grams of 2-anilino-3-hydroxy-4-(phenylimino)-2-cyclobuten-1-one and 3.8 grams of 1-propylpiperazine is heated in an atmosphere of dry nitrogen at 193° C. for 20 minutes. The reaction mixture is cooled to give an orange-brown solid which is comminuted under 40 ml. of anhydrous ethyl ether. The comminuted solid is separated by filtration, washed by suspension in 40 ml. of anhydrous ethyl ether, again separated by filtration, and dried in a steam cabinet. The product obtained in this way is 1-[2-hydroxy-3-(4-propyl-1-piperazinyl)-4-oxo-2-cyclobuten-1-ylidene]-4-propylpiperazinium hydroxide inner salt melting at about 197°–199° C. This compound has the following structural formula

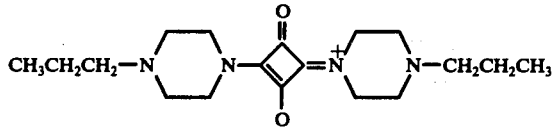

EXAMPLE 2

To a solution of 1.0 gram of 1-[2-hydroxy-3-(4-propyl-1-piperazinyl)-4-oxo-2-cyclobuten-1-ylidene]-4-propylpiperazinium hydroxide inner salt, 0.9 gram of concentrated hydrochloric acid and 15 ml. of distilled water, there is added 150 ml. of acetone with stirring. A microcrystalline solid precipitates. This is separated by filtration, washed with acetone and dried in a steam cabinet to give 1-[2-hydroxy-3-(4-propyl-1-piperazinyl)-4-oxo-2-cyclobuten-1-ylidene]-4-propylpiperazinium hydroxide inner salt dihydrochloride dihydrate melting at about 300°–350° C. with decomposition.

EXAMPLE 3

A mixture of 4.0 grams of 2-anilino-3-hydroxy-4-(phenylimino)-2-cyclobuten-1-one and 3.4 grams of 1-ethylpiperazine is heated at 194°–198° C. in an atmosphere of dry nitrogen for 30 minutes. The cooled solid is comminuted, washed with anhydrous ethyl ether, and dried and the resulting solid is then extracted with 50 ml. of anhydrous benzene. The benzene solution is treated with activated carbon, filtered, concentrated and cooled. A crystalline solid forms and this is separated by filtration and dissolved in distilled water at room temperature and the solution is filtered and concentrated. A precipitate forms and is separated by filtration to give 1-[2-hydroxy-3-(4-ethyl-1-piperazinyl)-4-oxo-2-cyclobuten-1-ylidene]-4-ethylpiperazinium hydroxide inner salt melting at about 179.5°–183° C.

EXAMPLE 4

A mixture of 4.0 grams of 2-anilino-3-hydroxy-4-(phenylimino)-2-cyclobuten-1-one and 3.9 grams of 1-isopropylpiperazine is heated at 200°–206° C. in an atmosphere of dry nitrogen for 30 minutes. The mixture is cooled and the resulting solid is comminuted, washed with anhydrous ethyl ether, dried and then recrystallized from water to give 1-[2-hydroxy-3-(4-isopropyl-1-piperazinyl)-4-oxo-2-cyclobuten-1-ylidene]-4-isopropyl-piperazinium hydroxide inner salt melting at about 194.5°–196.5° C.

EXAMPLE 5

The procedure of Example i is repeated using 2.6 grams of 2-anilino-3-hydroxy-4-(phenylimino)-2-cyclobuten-1-one, 4.2 grams of 1-butylpiperazine, and a reaction temperature of 204°–206° C. for one hour. The product obtained is 1-[2-hydroxy-3-(4-butyl-1-piperazinyl)-4-oxo-2cyclobuten-1-ylidene]-4-butylpiperazinium hydroxide inner salt melting at about 214.5°–216.5° C. after recrystallization from 2-butanone.

If the above procedure is repeated using 1-hexylpiperazine in place of the 1-butylpiperazine, the product obtained is 1-[2-hydroxy-3-(4-hexyl-1-piperazinyl)-4-oxo-2-cyclobuten-1-ylidene]-4-hexylpiperazinium hydroxide inner salt.

EXAMPLE 6

A mixture of 2.6 grams of 2-anilino-3-hydroxy-4-(phenylimino)-2-cyclobuten-1-one, and 3.1 grams of 1-propylhomopiperazine is heated at 209°–215° C. in an atmosphere of dry nitrogen for 20 minutes. The reaction mixture is cooled to give an oily orange liquid which is dissolved in 200 ml. of distilled water and extracted with 200 ml. of ether. The aqueous solution is then treated with activated carbon, filtered and concentrated to give an orange gum. The gum is extracted with 200 ml. of refluxing hexane and the hexane solution is concentrated and cooled in a dry ice-acetone bath. The precipitate which forms is separated by filtration to give 1-[2-hydroxy-3-(4-propl-1-homopiperazinyl)-4-oxo-2-cyclobuten-1-ylidene]-4-propylhomopiperazinium hydroxide inner salts as flaky yellow crystals melting at about 88.0°–89.0° C. This compound has the following formula:

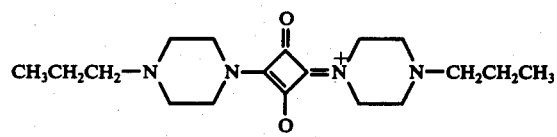

What is claimed is:
1. A compound of the formula

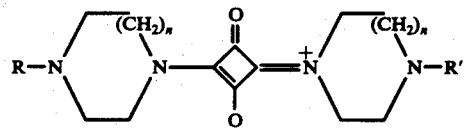

wherein R and R' are alkyl having from 2 to 6 carbon atoms and n is 1 or 2.

2. A compound according to claim 1 which has the formula

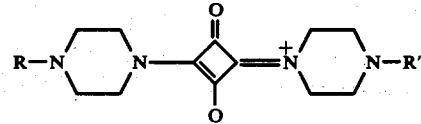

when R and R' are alkyl having from 2 to 6 carbon atoms.

3. A compound according to claim 1 which is 1-[2-hydroxy-3-(4-ethyl-1-piperazinyl)-4-oxo-2-cyclobuten-1-ylidene]-4-ethylpiperazinium hydroxide inner salt.

4. A compound according to claim 1 which is 1-[2-hydroxy-3-(4-propyl-1-piperazinyl)-4-oxo-2-cyclobuten-1-ylidene]-4 -propylpiperazinium hydroxide inner salt.

5. A compound according to claim 1 which is 1-[2-hydroxy-3-(4-butyl-1-piperazinyl)-4-oxo-2-cyclobuten-1-ylidene]-4-butylpiperazinium hydroxide inner salt.

* * * * *